US00PP20300P2

(12) United States Plant Patent
Keogh

(10) Patent No.: US PP20,300 P2
(45) Date of Patent: Sep. 15, 2009

(54) ***CUPHEA* PLANT NAMED 'FLAMENCO CHA CHA'**

(50) Latin Name: *llavea×procumbens*
Varietal Denomination: Flamenco Cha Cha

(76) Inventor: Terry Keogh, 209 Bunker Road, Victoria Point, Queensland (AU), 4165

( * ) Notice: Subject to any disclaimer, the term of this patent is extended or adjusted under 35 U.S.C. 154(b) by 8 days.

(21) Appl. No.: 12/151,957

(22) Filed: May 12, 2008

Related U.S. Application Data

(60) Provisional application No. 60/003,985, filed on Nov. 20, 2007.

(51) Int. Cl.
*A01H 5/00* (2006.01)

(52) U.S. Cl. ..... Plt./420

(58) Field of Classification Search ..... Plt./420
See application file for complete search history.

*Primary Examiner*—Annette H Para

(57) ABSTRACT

A new cultivar of *Cuphea* named 'Flamenco Cha Cha' that is characterized by dense upright habit, dark green foliage, and large bright magenta flowers that bloom continuously throughout spring, summer and fall. In combination these traits set 'Flamenco Cha Cha' apart from all other existing varieties of *Cuphea* known to the inventor.

2 Drawing Sheets

Genus: *Cuphea.*
Species: *llavea×procumbens.*
Denomination: 'Flamenco Cha Cha'.

BACKGROUND OF THE INVENTION

The present invention relates to a new and distinct cultivar of *Cuphea* that is grown for use as an annual plant for container or for use as a perennial plant for the landscape in frost-free regions. The new cultivar is known botanically as *Cuphea llavea×procumbens* and will be referred to hereinafter by the cultivar name 'Flamenco Cha Cha'.

The new *Cuphea* cultivar 'Flamenco Cha Cha' is a hybrid plant that resulted from the induced cross-pollination conducted by the inventor in June 2001 at the inventor's nursery in Brisbane, Queensland, Australia. 'Flamenco Cha Cha' was selected by the inventor in December 2003 based on upright habit, and dark red flowers with six lobes per individual flower.

The inventor cross-pollinated an individual plant of the seed parent, *Cuphea llavea* 'Tiny Mice' (unpatented) and an individual plant of the pollen parent *Cuphea procumbens* (species, not a cultivar, unpatented). Observing that the resulting seedlings exhibited a range of flower colors and flower shapes, the inventor set aside several hundred of these seedlings for further growth trials in order to select the most promising combination of unique flower shape, flower color, and compactness, of plant habit. Four individual clones, from the seedling population were selected by the inventor in 2003. One selection constitutes the present invention, 'Flamenco Cha Cha'. The other three selections are 'Flamenco Samba' (U.S. Plant Pat. No. 17,823), 'Flamenco Rumba' (U.S. Plant Pat. No. 17,213), and 'Flamenco Tango' (U.S. Plant Pat. No. 17,285).

'Flamenco Cha Cha' exhibits dense upright habit, large hairy flower buds, large deep magenta flowers and dark yellow-green foliage. Propagation is accomplished using vegetative cuttings. The closest comparison plant known to the inventor is the inventor's co-pending variety 'Flamenco Samba', which exhibits dark red flowers and an open upright habit. 'Flamenco Cha Cha' is distinguishable from the comparison plant by dark magenta flowers.

The new cultivar 'Flamenco Cha Cha' is distinguishable from the seed parent by flower color and number of lobes on an individual flower. The seed parent 'Tiny Mice' bears small orange flowers that individually exhibit two identical, fused lobes, whereas 'Flamenco Cha Cha' exhibits dark red flowers with six sub-equal lobes on an individual flower. 'Flamenco Cha Cha' is distinguishable from the pollen parent by flower color and plant habit. *Cuphea procumbens* exhibits spreading habit and bears purple flowers, whereas 'Flamenco Cha Cha' exhibits dense upright habit and dark magenta flowers.

The first asexual propagation was conducted by the inventor in 2003 at the inventor's nursery in Brisbane, Australia. The method of propagation used for asexual propagation was vegetative cuttings. Since that time, the distinguishing characteristics of 'Flamenco Cha Cha' have been determined stable and have been determined stable and reproduced true to type in successive generations of asexual reproduction.

SUMMARY OF THE INVENTION

The following represent the distinguishing characteristics of the new *Cuphea* cultivar 'Flamenco Cha Cha'. In combination these traits set 'Flamenco Cha Cha' apart from all other existing varieties of *Cuphea* known to the inventor. 'Flamenco Cha Cha' has not been tested under all possible conditions and phenotypic differences may be observed with variations in environmental, climatic, and cultural conditions, however, without any variance in genotype.

1. *Cuphea llavea×procumbens* 'Flamenco Cha Cha' exhibits large dark magenta flowers.
2. The flowers of *Cuphea llavea×procumbens* 'Flamenco Cha Cha' bloom continuously throughout spring, summer and fall.
3. *Cuphea llavea×procumbens* 'Flamenco Cha Cha' is an annual plant for container, or a perennial plant in frost-free regions.

4. *Cuphea llavea×procumbens* 'Flamenco Cha Cha' is readily propagated using vegetative cuttings.
5. *Cuphea llavea×procumbens* 'Flamenco Cha Cha' exhibits dense, upright habit.
6. *Cuphea llavea×procumbens* 'Flamenco Cha Cha' exhibits large hairy flower buds.
7. *Cuphea llavea×procumbens* 'Flamenco Cha Cha' is recommended for use in hanging basket, window box, clay container, and as a border plant in the landscape.
8. *Cuphea llavea×procumbens* 'Flamenco Cha Cha' exhibits short internodes, and dark yellow-green foliage.
9. *Cuphea llavea×procumbens* 'Flamenco Cha Cha' is hardy to USDA Zone 10.
10. *Cuphea llavea×procumbens* 'Flamenco Cha Cha' is 40 cm in height and 44 cm in width at maturity.

BRIEF DESCRIPTION OF THE DRAWINGS

The accompanying color drawings illustrate the overall appearance of the new *Cuphea* variety 'Flamenco Cha Cha' showing the colors as true as it is reasonably possible to obtain in colored reproductions of this type. Colors in the drawings may differ from the color values cited in the detailed botanical description, which accurately describe the actual colors of the new variety 'Flamenco Cha Cha'. The plant depicted in the drawings is 9 months old.

The drawing labeled

The drawing labeled

Figure 1:
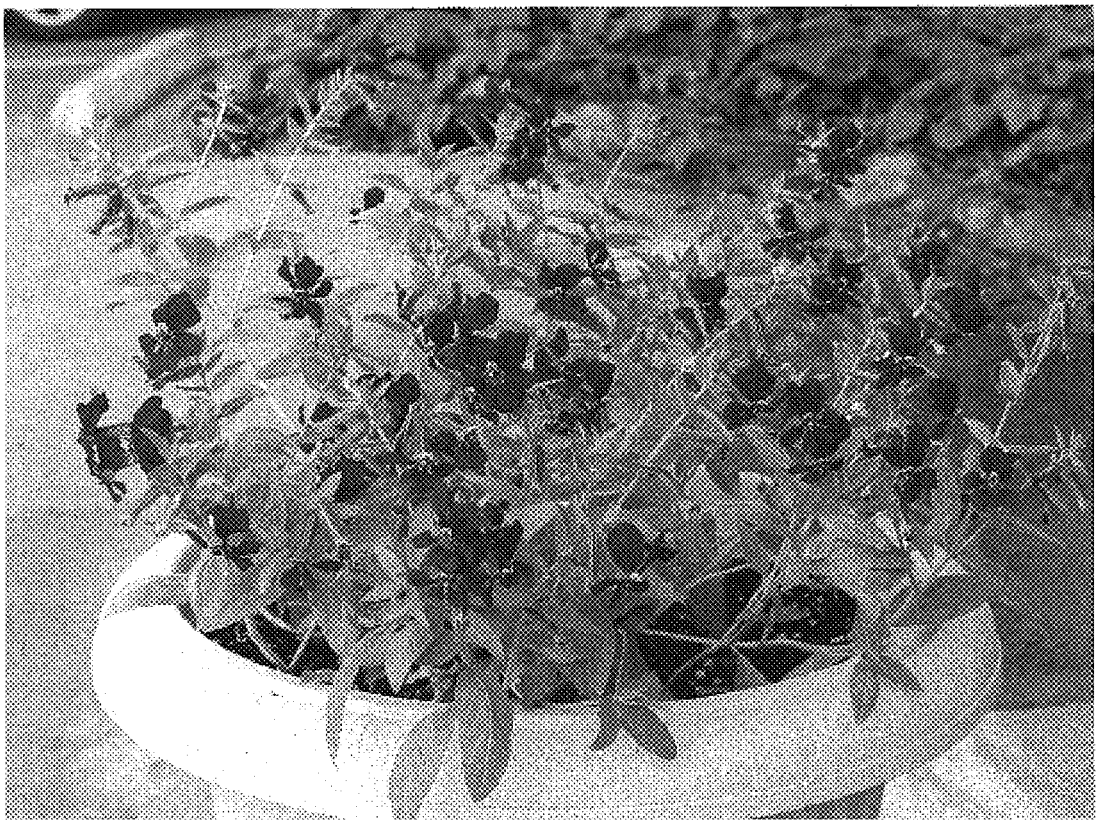
FIG. 1 depicts an entire plant in bloom from a side perspective.
Figure 2:
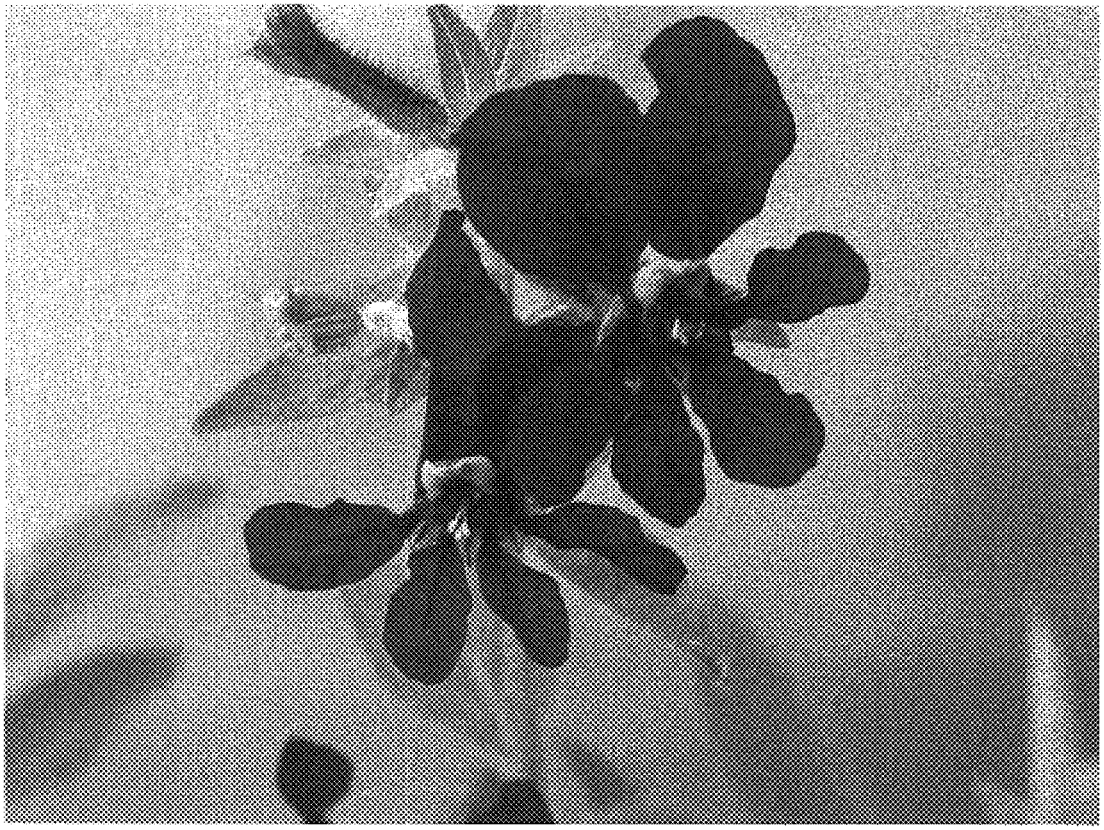
FIG. 2 depicts a close-up view of flowers and seed pods.

All drawings are made using conventional techniques and although foliage colors may appear different from actual colors due to light reflectance, they are as accurate as possible by conventional photography.

BOTANICAL DESCRIPTION OF THE PLANT

The following is a detailed description of the *Cuphea* cultivar named 'Flamenco Cha Cha'. Data was collected and compiled in Santa Barbara, Calif. from 2-liter container plants that were 9-months-old at the time. Color determinations are in accordance with The 2001 Royal Horticultural Society Colour Chart except where general color terms of ordinary dictionary significance are used. The growing requirements are similar to the species.

Botanical classification: *Cuphea llavea×procumbens* 'Flamenco Cha Cha'.
Genus: *Cuphea.*
Plant species: *llavea×procumbens.*
Denomination: Flamenco Cha Cha.
Common name: *Cuphea.*
Suggested uses: Recommended for use in hanging basket, window box, container, and as a border plant in the landscape.
Plant parentage: *Cuphea llavea×procumbens* 'Flamenco Cha Cha' is a hybrid plant that resulted from the induced cross-pollination of the following parent plants:
- *Seed parent.*—An individual *Cuphea llavea* 'Tiny Mice'.
- *Pollen parent.*—An individual *Cuphea procumbens.*

Plant type: An annual for use in container and a perennial for the landscape in frost-free regions.
Commercial category: Annual bedding plant; perennial in frost-free zones.
Recommended commercial container size: 2-liter commercial container.
Plant vigor: Moderate.
Plant habit: Dense, upright.
Plant dimension (at maturity): 35 cm in height and 40 cm in width.
Plant hardiness: Hardy to USDA Zone 10.
Plant propagation: Readily propagated using vegetative cuttings.
Root system: Fleshy root system.
Cultural requirements: Plant in full sun, using rich, well-draining potting soil, with regular watering.
Time to initiate rooting: 4–6 weeks are needed to produce roots on an initial cutting.
Crop time: 9–12 months are needed to produce a finished 2-liter container from a rooted cutting.
Seasonal interest: Large dark magenta flowers that bloom continuously throughout spring, summer and fall.
Disease and pests: None known to the inventor.
Special growing considerations: Use a slow release fertilizer once a season and a water-soluble fertilizer twice a month.
Stem:
- *Basal trunk.*—One in number.
- *Basal trunk color.*—N199A.
- *Basal trunk surface.*—Pubescent.
- *Basal trunk shape.*—Cylindrical.
- *Basal trunk diameter.*—0.75 cm.
- *Basal trunk height.*—1.50 cm.
- *Stem surface.*—Villous.
- *Color of villi.*—156B.
- *Stem shape.*—Cylindrical.
- *Stem color.*—144C.
- *Stem diameter.*—0.25 cm.
- *Stem length.*—10 cm to 18 cm.
- *Branching pattern.*—Divergent.

Foliage:
- *Leaf type.*—Evergreen.
- *Internode length.*—Internode averages 1 cm–2 cm.
- *Leaf arrangement.*—A combination of alternate, opposite and whorled.
- *Leaf division.*—Simple.
- *Leaf quantity.*—An average of 60 leaves.
- *Leaf shape.*—Oval.
- *Leaf base.*—Oblique.
- *Leaf apex.*—Acute.
- *Leaf venation pattern.*—Pinnate.
- *Vein color* (*abaxial and adaxial surfaces*).—138D.
- *Leaf surface* (*adaxial*).—Sparsely hispid.
- *Leaf surface* (*abaxial*).—Sparsely hispid.
- *Leaf texture* (*abaxial and adaxial surfaces*).—Bristly.
- *Leaf attachment.*—Both sessile and petiolate.
- *Petiole dimensions.*—4 mm in length and 1 mm in width.
- *Petiole shape.*—Cylindrical.
- *Petiole color.*—138B.
- *Petiole surface.*—Glabrous surface.
- *Stipules.*—None observed.
- *Leaf margin.*—Minutely toothed leaf.
- *Leaf color* (*adaxial surface*).—137B.
- *Leaf color* (*abaxial surface*).—137C.
- *Leaf length.*—2 cm to 4 cm.
- *Leaf width.*—0.75 cm to 2 cm.
- *Foliar fragrance.*—None observed.

Flower:
- *Blooming season.*—Continuously throughout spring, summer and fall.

*Inflorescence type.*—Raceme.
*Quantity of flowers.*—3–8 flowers per raceme.
*Flower shape.*—Closest to salverform.
*Corolla.*—None observed.
*Hypanthium.*—Conspicuous.
*Flower aspect.*—Facing upward and outward.
*Flower color.*—Individual colors 71A, N77A present.
*Flowers self-cleaning or persistent.*—Self-cleaning.
*Pedicel color.*—138B.
*Pedicel shape.*—Cylindrical.
*Pedicel length.*—2 mm.
*Pedicel width.*—1 mm.
*Pedicel surface.*—Pubescent.
*Flower bud shape.*—Cylindrical.
*Flower bud surface.*—Combination of villous and multicostate.
*Color of villi.*—156B.
*Flower bud texture.*—Viscidulous.
*Flower bud colors.*—Colors N92A, 156B, and 138A all present.
*Flower bud apex.*—Closest to truncate, and enclosing 6 crumpled valvate lobes.
*Flower bud base.*—Combination of gibbous and oblique.
*Flower bud dimensions.*—2 cm in length and 0.50 cm in diameter.
*Flower diameter.*—3 cm in width (across) and 4 cm in height (up and down).
*Flower depth.*—2.50 cm.
*Corolla tube diameter.*—0.50 cm.
*Corolla tube length.*—2.00 cm.
*Corolla tube color* (*ventral surface*).—138D and 73A.
*Corolla tube color* (*dorsal surface*).—N92A, 156B, 138A.
*Corolla tube shape.*—Tubular.
*Corolla tube apex.*—Flared.
*Corolla tube base.*—Combination of gibbous and oblique.
*Corolla tube surface* (*ventral and dorsal surfaces*).—Combination of villous and multicostate.
*Corolla tube texture.*—Viscidulous.
*Petals.*—Apetalous.
*Calyx.*—(Sepals form valvate lobes). Valvate lobe number: 6; 4 small lobes and 2 large lobes are present on an individual flower. Valvate lobes attachment: Individual valvate lobes are attached at summit of hypanthium. Valvate lobe arrangement: Rotate arrangement. Large valvate lobe dimensions: 1.40 cm in width and 1.50 cm in length. Small valvate lobe dimensions: 0.75 cm in width and 1 cm in length. Valvate lobe color (adaxial and abaxial surfaces): Colors 71A are present on an individual valvate lobe. Valvate lobe texture: Delicate. Valvate lobe surfaces (adaxial and abaxial surfaces): Rugose surfaces. Valvate lobe appearance (adaxial and abaxial surfaces): Irridescent. Valvate lobe shape: 2 individual valvate lobes are orbicular in shape and 4 individual valvate lobes are rotund in shape. Valvate lobe apex: Obtuse and rounded. Valvate lobe base: Cuneate and rounded. Valvate lobe margin: Valvate lobe margin is sinuous. Valvate lobes unfused or fused: Unfused.
*Flower fragrance.*—None observed.

Reproductive organs:
*Stamens.*—8 in number, semi-exserted and adnate to ventral surface of an individual corolla tube.
*Color of stamens.*—145D.
*Stamen dimensions.*—4 stamens are 1 cm in length and 4 stamens are 0.75 cm in length on an individual flower.
*Anthers.*—On an individual flower the long stamens are tufted with dense purple hairs and the short stamens exhibit anthers.
*Color of hairs.*—77D.
*Anther dimensions.*—0.75 mm in length and 0.75 mm in width.
*Anther color.*—83A.
*Amount of pollen.*—Minimal amount.
*Pollen color.*—150B.
*Pistil.*—One.
*Pistil length.*—2.50 cm.
*Pistil shape.*—Filament.
*Pistil surface.*—Puberulent.
*Pistil color.*—145D.
*Stigma color.*—145D.
*Stigma shape.*—Uncinate.
*Stigma dimensions.*—0.25 mm in length.
*Ovary position.*—Superior.
*Ovary shape.*—Ovate.
*Ovary color.*—145D.
*Ovary surface.*—Glabrous.
*Ovary dimensions.*—1 cm in height and 0.50 cm in width.

Seed:
*Number of seed.*—15–20 individual seeds.
*Seed shape.*—Discoid.
*Seed color.*—145D.
*Seed surface.*—Combination of glabrous and semi-glossy.
*Seed dimensions.*—1 mm.

What is claimed is:

1. A new and distinct variety of *Cuphea* plant named 'Flamenco Cha Cha' as described and illustrated herein.

* * * * *